United States Patent [19]

Blümcke et al.

[11] 4,436,823

[45] * Mar. 13, 1984

[54] SILICA GELS INCORPORATING INSOLUBILIZED REAGENTS

[75] Inventors: Alfred Blümcke; Peter Fischer, both of Rheinfelden; Hans-Joachim Vahlensieck, Wehr, all of Fed. Rep. of Germany

[73] Assignee: Dragerwerk Aktiengesellschaft, Lubeck, Fed. Rep. of Germany

[*] Notice: The portion of the term of this patent subsequent to Nov. 17, 1998 has been disclaimed.

[21] Appl. No.: 267,162

[22] Filed: May 26, 1981

Related U.S. Application Data

[62] Division of Ser. No. 54,518, Jul. 3, 1979, Pat. No. 4,301,027.

[30] Foreign Application Priority Data

Jul. 3, 1978 [DE] Fed. Rep. of Germany ....... 2829091

[51] Int. Cl.$^3$ ..................... C09K 3/00; G01N 31/22; G01N 21/06
[52] U.S. Cl. .................... 436/169; 252/408.1; 422/55; 422/56; 422/57; 436/527; 436/73; 436/163; 436/166; 436/183
[58] Field of Search ............. 422/55, 56, 57; 252/408.1; 436/527, 73, 163, 166, 169, 183

[56] References Cited

U.S. PATENT DOCUMENTS

| 2,929,829 | 3/1960 | Morehouse | 252/408.1 |
| 3,642,449 | 2/1972 | Novak et al. | 422/56 |
| 3,697,225 | 10/1972 | Schmitt et al. | 422/56 |
| 3,730,688 | 5/1973 | Schmitt et al. | 422/56 |
| 3,843,325 | 10/1974 | Schmitt et al. | 422/56 |
| 3,904,373 | 9/1975 | Harper | 422/56 |
| 3,966,897 | 6/1976 | Renn et al. | 422/56 |
| 4,022,578 | 5/1977 | Kretschmer | 422/57 |
| 4,203,952 | 5/1980 | Hancock et al. | 422/56 |
| 4,301,027 | 11/1981 | Blumcke et al. | 422/56 |

FOREIGN PATENT DOCUMENTS

| 3018257 | 11/1981 | Fed. Rep. of Germany | 422/56 |
| 54-134489 | 10/1979 | Japan | 422/56 |
| 1530039 | 10/1978 | United Kingdom | 252/408.1 |
| 1532295 | 11/1978 | United Kingdom | 252/408.1 |

OTHER PUBLICATIONS

Patterson, G. D., et al., Anal. Chem., vol. 24, No. 10, pp. 1586–1590, (1952).
Harper, C. B., Anal. Chem., vol. 47, No. 2, pp. 348–351, (1975).

Primary Examiner—Teddy S. Gron
Attorney, Agent, or Firm—Sprung, Horn, Kramer & Woods

[57] ABSTRACT

A dried silica gel containing a reagent in insolubilized form which reagent is normally soluble, especially a dried silica gel containing an insolubilized form of a normally soluble colorimetric analytical agent and a method of preparing such dried silica gel by hydrolyzing a silane having from 1 to 4 alkoxy groups in a homogeneous phase in the presence of a reagent which is normally soluble in a solvent, recovering the resultant gel and drying the same.

12 Claims, No Drawings

SILICA GELS INCORPORATING INSOLUBILIZED REAGENTS

This is a division of application Ser. No. 054,518, filed July 3, 1979, now U.S. Pat. No. 4,301,027.

BACKGROUND OF THE INVENTION

1. Field of the Invention

This invention relates to silica gels containing within their structure in insolubilized form reagents which are normally soluble. More especially, this invention relates to silica gels containing physico-chemically absorbed, in reactive but insolubilized form, reagents which can react with certain materials to be detected with evolution of color. More especially, this invention relates to silica gels containing reactive but insolubilized colorimetric analytical reagents which are normally soluble in solution. This invention further relates to the method for preparing such gels and their use in analysis or in the selective separation of cations and anions from an aqueous phase.

2 Discussion of the Prior Art

A great many organic and inorganic reagents have been described in the literature which can be used in analytical chemistry for the determination of cations and anions in the liquid phase, and preferably in an aqueous phase, and which in the presence of the ion in question give colored precipitates or corresponding color reactions. These reactions may be used both for qualitative and quantitative determination of the particular ion. However, the use of these methods calls for a properly equipped laboratory and trained laboratory personnel and is rather time-consuming.

Thus, there has been a need for simplifying these analytical detection and determination procedures and for adapting them so that they can be carried out anywhere.

SUMMARY OF THE INVENTION

It has now been found that the foregoing need can be met in accordance with the present invention which provides a dried silica gel containing within the structure insolubilized reactive reagent which reagent is normally soluble. In accordance with this invention it has been found that a wide variety of reagents both organic, inorganic and mixed, e.g., organometallic, which are soluble in an aqueous or organic solution can be incorporated in a silica gel in insolubilized but reactive form. As such, the reagents can be employed to react with the materials with which they normally react but in the solid phase.

More especially, it has been found that reagents which react with other materials with evolution of color, i.e., colorimetric analytical reagents, can be incorporated in a silica gel structure in insolubilized but still reactive form. These reagents which are normally soluble in other solvents such as water and organic solvents can be retained in the silica gel structure in insolubilized form where they can be employed for analytical purposes. Thus, the present invention relates to insolubilizing known soluble compounds used in analytical determinations of anions and cations and then using the resultant insolubilizate for analytical purposes. The insolubilizate is a silica gel which incorporates the compounds in question which as such are soluble but are in the insolubilizate fixed in such a way that they can no longer be washed out by solvents in which they are normally soluble. The new silica gels are characterized in that they contain these reagents in insolubilized but reactive form, the reagents being normally soluble.

These new silica gels can be prepared by hydrolyzing silanes having from 1 to 4 alkoxy groups, or their partial-condensation products, in the presence of these reagents, present in a solution, and then drying the gels so obtained. Once the gels have been dried, the reagents cannot be washed out of them. The reagent, originally soluble in a solvent, is permanently fixed in the gel. Surprisingly, however, it nevertheless exhibits its usual reactivity so that when the gel is wetted with appropriate cation- or anion-containing liquids the color reactions which usually are observed only in the liquid phase occur also in the silica gel. It thus becomes possible to carry out the analytical procedures which heretofore have been confined to stationary facilities anytime and anywhere without the use of special laboratory equipment or reagent solutions.

The distribution of the reagents in the new gels is extremely uniform, and the color reactions therefore also proceed absolutely uniformly in these gels.

When, on the other hand, commercial silica gels are conventionally impregnated with such reagents, the latter can again be washed out completely or at least partially after drying. Moreover, with this conventional procedure the distribution of the reagents over the silica gel is quite nonuniform and the reactivity which they are known to exhibit in the aqueous phase is lost in whole or in part.

The new special gels are preferably prepared by hydrolyzation of liquid silanes having from 1 to 4 alkoxy groups, or polysilicic acid esters, in the presence of colorimetric analytical reagents dissolved in water, alcohol or another organic solvent in homogeneous phase by the addition of acids or alkalis with careful stirring, the gel so obtained then being dried. Drying may be followed by size reduction, pulverization and screening.

By silanes having from 1 to 4 alkoxy groups are meant tetraalkyl orthosilicates or their condensation products or alkylalkoxysilanes of the general formula $$(RO)_{4-n}Si\ (R'X)_n\ (n=1-3)$$

wherein R represents alkyl radicals with from 1 to 4 carbon atoms, and R' represents an alkylene moiety with from 1 to 6 carbon atoms or the aryl radical —C$_6$H$_6$—. X is a moiety from the group consisting of hydrogen,

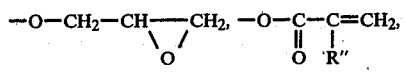

R" representing H or CH$_3$ or C$_2$H$_5$, and

wherein Z$_1$=H or —(CH$_2$)$_m$—NH$_2$ (m=2-4) or —[(CH$_2$)$_p$NH—(CH$_2$)$_p$]NH$_2$ (each p=1 or 2) and Z$_2$ may be one of the Z$_1$ moieties or H.

The gels in accordance with the invention will also be obtained when X is another radical such as halogen —COOH—, —SH, —OH, and R'X is the vinyl radical.

In these cases, n should be equal to 1. Mixtures of these silanes may also be used, especially when one of the components of the mixture is a tetraalkoxysilane.

The tetraalkyl orthosilicates which may be used as starting products are also called orthosilicic acid esters. While the alkyl group of the ester component may have up to 8 carbon atoms, $C_1$ to $C_4$ esters are preferably used.

The condensation products of silicic acid esters which may also be used as starting products for the new silica gels are condensation products obtained by incomplete hydrolysis or orthosilicic acid esters. They are also called polysilicic acid esters. The ester component in these compounds may have from 1 to 4 carbon atoms. These partial hydrolyzates contain up to 10, and preferably contain about 3 to 5, Si—O—Si bonds, and their $SiO_2$ content ranges from 35 to 52 percent. The $SiO_2$ content of the polysilicic acid methyl esters is about 50 percent, and that of the polysilicic acid ethyl esters between 38 and 42 percent. The polysilicic acid propyl and butyl esters which may be used have a correspondingly lower $SiO_2$ content.

For the preparation of the new silica gels, the hydrolysis of the organooxysilanes is carried out in a manner which as such is known. A weakly alkaline or weakly acidic medium is preferably used to obtain as nearly quantitative conversion as possible. Suitable alkalis or acids are such compounds as $NH_3$, hydrochloric acid or oxalic acid which can be metered in particularly readily. Generally, the pH of the aqueous solutions used for hydrolysis is 4 to 9. Additional heating of the solution to be hydrolyzed is not necessary. Since the hydrolysis reaction is exothermic, it evolves heat. During the hydrolysis, a gel is produced which may be dried either immediately or after a water wash and which may then be ground.

In principle, the new silica gels may incorporate any of the known organic or inorganic reagents and/or organometallic compounds soluble in water or in organic solvents. The organic solvents in which the reagents suitable for use should preferably be soluble are alcohols, and preferably methanol and ethanol, or ketones such as acetone. Once the reagents have been incorporated in the silica gel, they are no longer soluble in these solvents.

The reagents which may be incorporated include the compounds which as such are known for the detection or determination or fixation of anions or cations from a liquid medium. In principle, all reagents soluble in solvents are suitable, regardless of their constitution and of the functional groups present. Such reagents are described in the book "TUMLu/ pfelanalyse" (Spot analysis) by Feigl, for example, or in the book "Organische Reagenzien Merck für die anorganische Analyse" (Organic Merck reagents for inorganic analysis), published by Verlag Chemie, Weinheim, the disclosures of which are hereby incorporated specifically herein by reference.

Suitable for incorporation in the new silica gels are, therefore, in addition to inorganic compounds such as alkali rhodanide, complex iron cyanides, alkali sulfides or ammonium molybdate, aliphatic, aromatic or heterocyclic compounds such as:

The disodium salt of rhodizonic acid: (for $Pb^{++}$ detection)
2,2'-Bipyridine: (for $Fe^{++}$ detection)
Dimethylglyoxime: (for $Ni^+$ detection)
Diphenyl carbazide: (for $Hg^{++}$, $CrO_4^{--}$ and $Cr_2O_7^{--}$ detection)
α-Benzoinoxime: (for $Cu^{++}$ detection)
Salicylaldoxime: (for $Fe^{++}$ detection)

Alizarins, rhodamines, anthraquinones, benzidine, brucine and other organic reagents for analytical purposes described in the literature may also be incorporated and insolubilized in silica gels in accordance with the invention. The new insolubilizates so obtained may likewise be used for analytical purposes.

Among the organometallic compounds which may be used are those of the formula

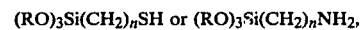
$$(RO)_3Si(CH_2)_nSH \text{ or } (RO)_3Si(CH_2)_nNH_2,$$

wherein R is a $C_1$ to $C_4$ alkyl radical and n has a value between 1 and 4.

Other reagents whch can be incorporated in the silica gel structure in reactive but insolubilized form include:
1,2-dihydroxianthraquinone as zirconium-complex (for $F^-$ detection)
Dithizone: (for $Zn^{++}$ detection)
Dithiol: (for $Sn^{++}$ detection)
Eriochromcyanin R: (for $Al^{+++}$ detection)
Benzidine: (for $NO_2^-$ detection)
Diphenylcarbazide: (for $Cd^{++}$ detection)

For analytical use, the new silica gels incorporating a precisely defined amount of the particular insolubilized organic reagent per unit weight of the silica gel are charged to columns in a manner appropriate to the particular use. When a defined amount of water containing the ion to be determined is passed through that column, the onset of the corresponding color reaction amounts to qualitative identification of the ion in question while the length of the color zone is a quantitative measure of the ion concentration.

Before the onset of the detection reaction, these special silica gels are often colorless, sometimes colored, depending on the original color of the organic reagents used.

The amount of the organic reagents to be incorporated in the gel depends on the desired threshold of detection. The lower the concentration of the organic reagent is, the lower the threshold of detection will be, the lower limit of detectability being determined by the intensity of the color reaction and the diameter of the column.

Since these detection reactions are extremely simple to carry out and thus can readily be carried out also by persons other than trained analysts, they are particularly well suited also for the many analyses which in the monitoring of bodies of water, waste waters, sewage-treatment plants, etc., for environmental protection reasons must often be performed outdoors. After a sample of the water has been taken, the respective analysis can be made right on the spot and the result read directly off the colored column.

However, these special gels may also be used for the preparatory separation of specific ions, in which case the concentration of the organic reagents in these gels should be as high as possible.

While a similar separation of a wide variety of ions can be achieved also with commercial ion exchangers, these give no indication by a color reaction and do not exhibit comparable selectivity.

Generally speaking, for use of the silica gel for qualitative analysis the normally soluble reactive analytical reagent should be present in the silica gel in an amount of between 0.5 and 5 weight percent, depending on the size of the molecule for which the reagent should be present in the hydrolyzing medium in an amount of 0.2 to 3 weight percent based upon the weight of the medium plus the silane.

When the resultant gel is to be used for quantitative analysis the same should contain the analytical reagent in an amount of 0.5 to 5 weight percent for which the same should be present in the mixture of silane and hydrolyzing medium in an amount of 0.2 to 3 weight percent.

Where it is to be used to separate ions, the concentration of colorimetric analytical reagent in the silica gel should be 5 to 20 weight percent for which the same should be present in the mixture of hydrolyzing medium and silane in an amount of 2 to 10 weight percent.

The examples which follow illustrate the preparation and the many uses of these new special silica gels.

EXAMPLE 1

2184 g tetramethoxysilane was charged to a 5-liter round-bottom flask. 1724 ml methanol and 5.7 g of the disodium salt of rhodizonic acid, dissolved in 1034 ml of water, were then introduced with stirring, a clear solution being thus obtained.

After the addition of 14 ml of a 25% ammonia solution, the temperature rose rapidly and within one minute reached about 42° C., with the entire solution gelling. After the stirrer had been turned off, the temperature continued to rise to 68° C. It was then allowed to drop to 30° C. and the reaction product was dried in a rotary evaporator at a bath temperature of 110° C. and a vacuum of from 1 to 20 millibars until a constant weight was obtained.

1000 g of a light-gray silica gel was obtained which with lead(II) salt solutions gave a dark-brown coloration.

EXAMPLE 2

1055 g tetramethoxysilane and 821 g isobutyl trimethoxysilane were charged to the flask of Example 1. 5.6 g of 2,2'-bipyridine, dissolved in 1670 ml of methanol, was then added and the mixture hydrolyzed with 1014 ml of an aqueous 0.3% ammonia solution. The temperature rose rapidly, reaching about 43° C. within approximately 20 sec. At the end of that time, the hydrolyzate obtained had gelled into a colorless mass, which then was processed further as described in Example 1. 1000 g of a silica gel was thus obtained which with iron(II) salt solutions gave a bright red coloration.

EXAMPLE 3

In accordance with the preceding examples, a mixture was prepared from 1040 g of tetramethoxysilane, 720 g of n-octyltrimethoxysilane, 1140 ml of methanol and 39.7 g of dimethylglyoxime, which has hydrolyzed with 1135 ml of an aqueous 0.3% ammonia solution. After the reaction mixture had gelled, it was worked up and dried as described in Example 1.

1000 g of a silica gel was thus obtained which with nickel(II) salt solutions gave an intense red coloration.

EXAMPLE 4

A solution was prepared from 1550 ml ethanol, 660 ml of 1% hydrochloric acid and 41.8 g dimethylglyoxime, which then was mixed with 2198 g of partly condensed ethyl silicate (40% $SiO_2$). The temperature of the slightly turbid mixture initially dropped from 20° to 18° C. and then rose within 8 min. to 34° C. At 32° C. the mixture was perfectly clear and colorless. After cooling to about 20° C., 1099 ml of an aqueous 1% ammonia solution was added. Within 10 sec, the mixture gelled into a solid, colorless mass, which was then worked up as described in Example 1.

1000 g of a colorless silica gel was so obtained which with nickel(II) salt solutions gave an intense red coloration.

EXAMPLE 5

A mixture was prepared from 2389 g tetramethoxysilane, 2358 ml of methanol and 31.4 g diphenyl carbazide, which was hydrolyzed with 1163 ml of an aqueous 0.3% ammonia solution. The mixture gelled at about 52° C. and after drying yielded 1000 g of a faintly pink-colored silica gel which with Hg(II) salt solutions gave a deep blue-violet coloration.

EXAMPLE 6

1480 g tetramethoxysilane and 636 g mercaptopropyltriethoxysilane were mixed and hydrolyzed with 780 ml of an aqueous 0.3% ammonia solution. The dried reaction product yielded 1000 g of a white silica gel, which with Co(II) salt solutions gave a deep-brown coloration.

EXAMPLE 7

2356 g tetramethoxysilane, 1085 ml ethanol and 38.5 g α-benzoinoxime were mixed. The mixtue was hydrolyzed with 1132 ml of an aqueous 0.3% ammonia solution. A gel was obtained which was dried in accordance with Example 1. Yield: 1000 g. Upon treatment with aqueous copper(II) salt solution, the white gel took on an intense green coloration.

EXAMPLE 8

2010 g of a partially condensed tetramethoxysilane was mixed with 51% $SiO_2$, 1750 ml methanol and 5.9 g diphenyl carbazide. The mixture was hydrolyzed with 914 ml of an aqueous 0.3 ammonia solution. After drying, 1000 g of a faintly pink-colored silica gel was obtained which with acetic chromate solutions gave deep-violet colorations.

EXAMPLE 9

A mixture of 2282 g tetramethoxysilane, 750 ml methanol and 37.5 g salicylaldoxime was hydrolyzed with 1095 ml of an aqueous 0.3% ammonia solution. After drying, 1000 g of a colorless silica gel was obtained which with iron(III) salt solutions gave a brown coloration.

EXAMPLE 10

2317 g tetramethoxysilane and 1830 ml methanol were mixed. To this mixture a solution of 12.2 g potassium hexacyanoferrate(II) and 1098 g water was added. The slightly turbid mixture so obtained was hydrolyzed by the addition of 15.2 ml of concentrated ammonia solution. After drying, 1000 g of a greenish silica gel was obtained which with iron(III) salt solutions gave a blue coloration.

For actual use, the silica gels prepared in Examples 1 to 10 are ground and screened after drying. 1 g of the silica gel is then charged to a small glass tube 5.6 mm in diameter and 10 cm long whose lower end tapers into a funnel-like tip. When 1 ml of the solution or waste water to be analyzed is allowed to flow through this tube, the color change serves as qualitative identification of the ion in question while the length of the colored column is a quantitative measure of the concentration of that ion. The tube may be provided with appropriate gradations.

The silica gels prepared in Examples 1 to 10 may be used for the qualitative and quantitative identification by color change of the following ions, among others:

| Ex. | Identification of | Color of column before reaction | Color of column after reaction | Lowest threshold of detection | Length of colored column | Total capacity of column |
|---|---|---|---|---|---|---|
| 1 | $Pb^{++}$ | Light gray | Dark brown | 5 ppm | 0.5 mm | 6.0 mg Pb |
| 2 | $Fe^{++}$ | Colorless | Red | 1 ppm | 0.3 mm | 0.73 mg Fe |
| 3 | $Ni^{++}$ | Colorless | Red | 1 ppm | 0.8 mm | 11 mg Ni |
| 5 | $Hg^{++}$ | Pale pink | Dark blue/ Violet | 2 ppm | 0.8 mm | 14.2 mg Hg |
| 6 | $Co^{++}$ | Colorless | Dark brown | 0.2 ppm | 0.7 mm | 104 mg Co |
| 7 | $Cu^{++}$ | Colorless | Dark green | 1.5 ppm | 1.0 mm | 11.7 mg Cu |
| 8 | $CrO_4^{--}/Cr_2O_7$ | Pale pink | Dark violet | 0.3 ppm | 1.0 mm | 1.4 mg $CrO_4$ |
| 9 | $Fe^{+++}$ | Colorless | Brown | 10 ppm | 0.5 mm | 5.4 mg Fe |
| 10 | $Fe^{+++}$ | Greenish | Blue | 15 ppm | 0.5 mm | 2.6 mg Fe |

A major advantage of the invention described is that only about 1 ml of test liquid is required for such quantitative identifications and that the result can be read off directly, without auxiliary means.

The sensitivity of the method can be adapted to the requirements by variation of the concentration of the reagents in the silica gels and of the dimensions of the glass tubes.

By contrast to Examples 1 to 10, in the examples which follow higher concentrations of the reagents are incorporated in order to bind a larger amount of the ion in question to the silica gel, which of course is of major interest in the purification of special solutions or of waste waters.

EXAMPLE 11

2130 g tetramethoxysilane, 1120 ml methanol and 100 g of the disodium salt of rhodizonic acid are hydrolyzed with 1020 ml of an aqueous 0.3% ammonia solution. After drying, 1000 g of a gray silica gel is obtained which is capable of binding a total of 9.67 wt. % Pb, based on the dried silica gel, from a 1% $Pb^{++}$ salt solution.

EXAMPLE 12

2138 g tetramethoxysilane, 1145 ml methanol and 100 g dimethylglyoxime are hydrolyzed with 1024 ml of an aqueous 0.3% ammonia solution. After drying, 1000 g of a colorless silica gel is obtained which is capable of binding 2.52 wt. % Ni, based on the dried silica gel, from a 1% $Ni^{++}$ salt solution.

Depending on actual requirements, any desired reagents may be incorporated in these silica gels in high concentration in accordance with Examples 11 and 12.

We claim:

1. A composition consisting essentially of a dried silica gel containing in insolubilized form a normally soluble reagent which retains it reactivity, said reagent being uniformly absorbed in and throughout said silica gel, said reagent being insoluble to solvents in which it is normally soluble.

2. A composition according to claim 1 wherein said reagent is uniformly absorbed in and throughout said silica gel and is present in sufficient concentration that it reacts with reagents with which it normally reacts uniformly, said reagent being present in an amount of 0.5 to 5 percent by weight based upon the weight of said silica gel.

3. A composition according to claim 2 wherein said reagent is bound to said silica gel by hydrolysis.

4. A composition according to claim 1 wherein said reagent is a colorimetric analytical reagent.

5. A composition according to claim 4 wherein said analytical reagent is one which reacts with a metal in a test solution with evolution of color.

6. A composition according to claim 5 wherein said analytical reagent is an organic compound.

7. A composition according to claim 5 wherein said analytical reagent is an inorganic compound.

8. A composition according to claim 5 wherein said analytical reagent is an organometallic compound.

9. A composition according to claim 5 wherein said analytical reagent is an alizarin, a rhodamine, an anthraquinone, benzidene or brucine.

10. A composition according to claim 5 wherein said analytical reagent is the disodium salt of rhodizonic acid, 2,2'-bipyridine, dimethylglyoxime, diphenyl carbazide, α-benzoinoxime or salicylaldoxime.

11. A composition according to claim 5 wherein said analytical reagent is an alkali rhodanide, a complex iron cyanide, an alkali sulfide, or an ammonium molybdate.

12. A composition according to claim 5 wherein said analytical reagent is organometallic compound of the formula $$(RO)_3Si(CH_2)_nSH \text{ or } (RO)_3Si(CH_2)_nNH_2$$

where R is a $C_1$ to $C_4$ alkyl radical and n has a value between 1 and 4.

* * * * *

UNITED STATES PATENT AND TRADEMARK OFFICE
CERTIFICATE OF CORRECTION

PATENT NO. : 4,436,823

DATED : March 13, 1984

INVENTOR(S) : Alfred Blumcke et al

It is certified that error appears in the above-identified patent and that said Letters Patent is hereby corrected as shown below:

Col. 3, line 53 — Delete "TUMLu/pfelanalyse" and substitute --Tüpfelanalyse--

Col. 3, last line — Second column delete "$Ni^+$" and substitute --$Ni^{++}$--

Col. 6, line 30 — Delete "mixtue" and substitute --mixture--

Signed and Sealed this

Twelfth Day of March 1985

[SEAL]

Attest:

DONALD J. QUIGG

Attesting Officer     Acting Commissioner of Patents and Trademarks